United States Patent [19]

Saischek et al.

[11] Patent Number: 4,608,440
[45] Date of Patent: Aug. 26, 1986

[54] 1,3,2-DIOXABORINANES

[75] Inventors: Gerald Saischek, Wels; Hans Bodingbauer, Hellmonsödt, both of Austria

[73] Assignee: Chemie Linz Aktiengesellschaft, Linz, Austria

[21] Appl. No.: 696,760

[22] Filed: Jan. 31, 1985

[30] Foreign Application Priority Data

Feb. 7, 1984 [DE] Fed. Rep. of Germany ........ 3404253

[51] Int. Cl.$^4$ ............................................. C07F 7/22
[52] U.S. Cl. .......................................... 556/7; 71/97; 514/493
[58] Field of Search ............................................. 556/7

[56]       References Cited
       U.S. PATENT DOCUMENTS

| 2,904,569 | 9/1959 | Ramsden ................... 556/7 |
| 3,140,977 | 7/1964 | Duyfjes et al. |
| 3,312,725 | 4/1967 | Weissenberger .............. 556/7 |
| 3,497,537 | 2/1970 | Fish ......................... 556/7 |
| 3,657,451 | 4/1972 | Horne |
| 4,021,407 | 5/1977 | Gough et al. ............. 556/7 X |
| 4,035,403 | 7/1977 | Gough et al. ............... 556/7 |

FOREIGN PATENT DOCUMENTS 1178853 10/1964 Fed. Rep. of Germany.

OTHER PUBLICATIONS

Chemical Abstracts 78, 58553j (1973).
Chemical Abstracts 84, 106574q (1975).
Chemical Abstracts 81, 13586t (1974).

Primary Examiner—Helen M. S. Sneed
Attorney, Agent, or Firm—Mark Dryer

[57]        ABSTRACT

Novel 1,3,2-dioxaborinanes of the general formula

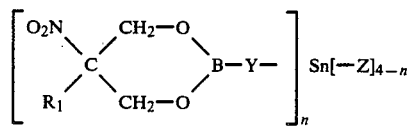

wherein $R_1$ is a straight-chain or branched alkyl group having 1 to 20 carbon atoms, a phenyl group or bromine, Y is a 1-oxy-2-thioethyl group, a 1-oxy-4-thiophenyl group or oxygen, each group Z independently of the others is a straight-chain or branched alkyl group having 1 to 20 carbon atoms, a cycloalkyl, bicycloalkyl or cycloalkylalkyl group, a phenyl group or a phenylalkyl radical, and n is the number 1 or 2. The compounds possess outstanding biocidal properties.

15 Claims, No Drawings

1,3,2-DIOXABORINANES

The invention relates to novel 1,3,2-dioxaborinanes, biocidal agents containing these compounds, and their use.

U.S. Pat. No. 3,140,977 discloses that triphenyl-tin compounds possess fungicidal properties. Furthermore, U.S. Pat. No. 3,657,451 discloses that trisneophyl-tin compounds can be used as acaricidal agents. German Pat. No. 1,178,853 discloses that boron-containing organo-tin mercapto compounds are suitable as stabilizers for polyvinyl chloride materials or as vulcanization or polymerization accelerators.

Surprisingly, it has now been found that certain 1,3,2-dioxaborinanes which are bonded in the 2-position to an organo-tin compound via the group Y possess outstanding biocidal properties.

The present invention accordingly relates to 1,3,2-dioxaborinanes of the general formula

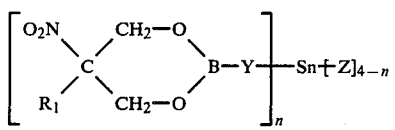

(I)

wherein $R_1$ is a straight-chain or branched alkyl group having 1 to 20 carbon atoms, a phenyl group or bromine, Y is a 1-oxy-2-thioethyl group, a 1-oxy-4-thiophenyl radical or oxygen, each group Z independently of the others is a straight-chain or branched alkyl group having 1 to 20 carbon atoms, a cycloalkyl, bicycloalkyl or cycloalkylalkyl group, a phenyl group or a phenylalkyl group, and n is the number 1 or 2.

Furthermore, it has been found that 1,3,2-dioxaborinanes of the general formula I are obtained if a diol of the general formula II

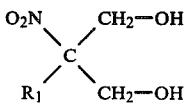

(II)

in which $R_1$ has the meaning given above, is reacted with an equivalent amount of boric acid or its anhydrides and, if required, with an equivalent amount of 2-mercaptoethanol or of 4-mercaptophenol at a temperature of 30° to 180° C., if appropriate in a diluent which is inert under the reaction conditions, with elimination of water, and, where n is 1, the reaction product is reacted with an equivalent amount of a compound of the general formula

 (III)

in which Z has the meaning given above, or with its anhydride, and, where n is 2, the reaction product is reacted with an equivalent amount of a compound of the general formula

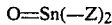 (IV)

in which Z has the meaning given above, with further elimination of water, at a temperature of 30° to 180° C., and, if required, the inert diluent is then removed.

The 1,3,2-dioxaborinanes according to the invention possess pronounced biocidal properties against a broad spectrum of harmful organisms and thus constitute an enrichment of the art.

In formula I, the group $R_1$ advantageously represents an alkyl group having 1 to 15 carbon atoms, in particular an alkyl group of 1 to 10 carbon atoms. Alkyl groups having 1 to 5 carbon atoms and bromine are particularly preferred. The group Y represents, in particular, oxygen. The groups Z advantageously represent a straight-chain or branched alkyl group of 1 to 10 carbon atoms, in particular an alkyl group of 1 to 5 carbon atoms, such as, for example, the butyl or neopentyl group. Furthermore, suitable cycloalkyl, bicycloalkyl or cycloalkylalkyl groups Z are, for example, the cyclohexyl, the norbornyl or the cyclohexylmethyl group, and suitable phenylalkyl groups Z are, for example, the benzyl and the 2,2-dimethyl-2-phenylethyl group, which is referred to below by the usual name of "neophyl" group. In addition to the neophyl group, the cyclohexyl group and the phenyl group are particularly preferred. The groups Z can be identical or different, but are preferably identical.

The 1,3,2-dioxaborinanes of the general formula I are advantageously prepared by reacting 1 mole of a diol of the general formula II with 1 mole of boric acid, and, if Y does not denote oxygen, with 1 mole of boric acid and with 1 mole of 2-mercaptoethanol or 4-mercaptophenol, to give the corresponding dioxaborinanes, the mercapto compound always reacting with the boric acid via the hydroxyl group, and the mercapto group remaining free. Where n is 1, the reaction product is then reacted with 1 mole of a compound of the general formula

 (III)

in which Z has the meaning given above, or with 0.5 mole of a compound of the general formula

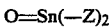 (IV)

in which Z has the meaning given above.

Instead of boric acid, it is also possible to use one of its anhydrides, such as metaboric acid or boron trioxide; the organic hydroxy-tin compounds of the general formula III can also be used in the form of the anhydride, as bis-(triorgano-tin) oxide.

The reaction steps can be carried out stepwise by reaction of the diol and the boric acid or by reaction of the diol, boric acid and hydroxy-mercapto compound followed by reaction with the tin compound. If a hydroxy-mercapto compound is not incorporated in the molecule, which is the case when Y denotes oxygen, it is particularly advantageous to allow all the reactants to react with one another simultaneously.

The reaction is advantageously carried out in a solvent or diluent which is inert for the reaction, for example at temperatures between 30° and 180° C., preferably between 60° and 120° C., under atmospheric pressure or slightly reduced pressure. Examples of suitable diluents are halogenated or non-halogenated aliphatic or aromatic hydrocarbons, such as gasoline fractions, benzene, chlorobenzenes, toluene, xylenes, chloroform or methylene chloride.

Since the overall reaction takes place with elimination of water, the end of the reaction can readily be determined from the amount of water of reaction formed; this water is removed from the reaction mixture by, for example, azeotropic distillation. When the reaction is complete, the diluent is removed by distillation under atmospheric pressure or, particularly advantageously, under reduced pressure, whereupon a viscous oily residue is generally formed, which can be used further without further purification steps.

The end of the reaction and complete conversion to the desired end compound are also evident from spectroscopic data: in the infrared spectrum, the adsorptions in the range of 650 to 800 cm$^{-1}$ (Sn—O—Sn bond) and in the range from 3,300 to 3,700 cm$^{-1}$ (free or associated stretching vibrations) vanish. The formation of the dioxaborinane ring is characterized by means of the $^1$H-NMR spectrum (100 MHz), the methylene protons of the ring producing a typical AB system with a coupling constant of J=12 Hz.

Exchangeable protons are no longer present.

The compounds can be further characterized as follows:

$z=(f_A+f_B)/2$: Center of resolution of the AB system or the methylene protons in the 1,3,2-dioxaborinane ring (in ppm)

$f_A-f_B$: Difference in the resonance frequencies of the AB system (in HZ).

The compounds according to the invention can be employed for the treatment of industrial materials and plants which suffer from a disease as a result of the action of algae, bacteria, fungi or insects, or are to be protected from these. Because of their fungicidal and algicidal activity, the agents can be employed for controlling harmful organisms from the classes comprising the Schizomycetes, Myxomycetes, Phycomycetes, Ascomycetes, Basidiomycetes and Deuteromycetes, and for controlling algae. For controlling insects and mites, in particular those of the order Acarina, particularly suitable agents according to the invention are those in which the groups R$_1$ and Y and the number n have the meaning given above, and each group Z independently of the others denotes a straight-chain or branched alkyl group having 1 to 20 carbon atoms, a cycloalkyl, bicycloalkyl or cycloalkylalkyl group or a phenylalkyl group. Examples of insects are insects of the orders Lepidoptera, Coleoptera, Neuroptera, Rhynchota, Copeognatha, Diptera, Thysanoptera, Orthoptera, Anoplura and Hymenoptera. Both plant-damaging mites, for example those of the families Tetranychidae, Tarsonemidae, Eryophyidae, Tyroglyphidae and Glycyphagidae, and ectoparasitic mites and ticks, for example those of the families Ixodidae, Argasidae, Sarcoptidae and Dermanyssidae, can be controlled in an outstanding manner.

The good toleration by plants, and the systemic activity in some cases in the concentrations necessary for the treatment of plant diseases, permit treatment of the above-ground parts of plants, of propagation stock, of seed and of the soil. Examples of plants are species of cereals, such as wheat, barley, rye or oats, rice, corn, cotton, soybean, coffee, sugarcane, sugarbeet, squash plants and Brassicae species.

The compounds according to the invention can be used with particularly good success, for example, for controlling the following plant diseases:

*Erysiphe graminis* in cereals
*Erysiphe betae* in sugarbeet
*Podosphaera leucotricha* in apples
*Uncinula necator* in vines
Puccinia species in cereals
Ustilago species in cereals
*Venturia inaequalis* in apples
*Septoria nodorum* in wheat
*Septoria apii* in celery
*Cercospora beticola* in sugarbeet
*Phytophthora infestans* in potatoes and tomatoes
*Peronospora viticola* in vines
*Alternaria solani* in potatoes
*Helminthosporium avenae* in barley
*Tilletia caries* in wheat When used in appropriate amounts, the substances can also be employed as wood preservatives against wood-discoloring fungi and wood-rot fungi, such as, for example, for controlling *Merulius Lacrimans, Polyporus vaporarius, Poria placenta* or *Polystictus cinnabarinus.* The agents according to the invention can also be used for controlling algae and slime in flooded agricultural crops, in industrial processes, in cooling plants and effluents, in greenhouses, lakes and rivers, swimming pools and aquaria, or as additives to building materials and plastics, glues, lacquers or other paints.

Depending on their field of use, the active ingredients can be converted to the conventional formulations, such as solutions, wettable powders, emulsion concentrates, emulsions, suspensions, powders, foams, pastes, granules, aerosols, natural and synthetic materials impregnated with active ingredient, very fine capsules in polymeric substances and in coating compositions for seed, and formulations used with burning equipment, such as fumigating cartridges, fumigating cans, fumigating coils and the like, as well as ULV cold mist and warm mist formulations.

These formulations can be produced in a known manner, for example by mixing the active ingredients with extenders, i.e. liquid solvents, liquefied gases under pressure, and/or solid carriers, if appropriate with the use of surfactants, i.e. emulsifiers and/or dispersants and/or wetting agents and/or foam-producing agents. Where water is used as an extender, it is also possible, for example, to use organic solvents as auxiliary solvents. Suitable liquid solvents are essentially aromatics, such as xylene, toluene or alkylnaphthalenes, chlorinated aromatics or chlorinated alphatic hydrocarbons, such as chlorobenzenes, chloroethylenes or methylene chloride, aliphatic hydrocarbons, such as cyclohexane or paraffins, for example mineral oil fractions, alcohols, such as butanol or glycol, and their ethers and esters, ketones, such as acetone, methyl ethyl ketone, methyl isobutyl ketone or cyclohexanone, strongly polar solvents, such as dimethylformamide and dimethyl sulfoxide, and water. By liquefied gaseous extenders or carriers are meant those liquids which are gaseous at normal temperatures and under atmospheric pressure, for example aerosol propellants, such as halohydrocarbons, as well as butane, propane, nitrogen and carbon dioxide; suitable solid carriers are, for example, ground natural minerals, such as kaolins, clays, talc, chalk, quartz, attapulgite, montmorillonite or diatomaceous earth, and synthetic products, such as highly disperse silica, alumina and silicates; suitable solid carriers for granules are, for example, crushed and fractionated natural rocks, such as calcite, marble, pumice, sepiolite and dolomite, and synthetic granules of inorganic and organic meals, and granules of organic material, such as sawdust, coconut shells, corn cobs and tobacco stalks; suitable emulsifiers and/or foam-forming agents are, for example, non-ionic and ionic surfactants, such as polyoxyethylene fatty acid esters, polyoxyethylene fatty alcohol ethers, for example alkylaryl polyglycol ethers, alkylsulfonates, alkylsulfates, arylsulfonates and arylalkylsulfonates, and protein hydrolysis products; suitable dispersants are, for example, ligninsulfonates and condensation products of arylsulfonates with formaldehyde.

Adhesives and thickeners, such as carboxymethylcellulose, methylcellulose, natural and synthetic polymers in the form of powders, granules or latices, such as gum arabic, polyvinyl alcohol and polyvinyl acetate, can be used in the formulations, and inorganic or organic colorants can be added to the formulations.

The formulations contain in general between 0.1 and 95% by weight of active ingredient, preferably between 0.5 and 90% by weight.

The active ingredients can be used as such, in the form of their formulations or in the use forms prepared therefrom by further dilution, such as ready-to-use solutions, emulsions, suspensions, powders, pastes and granules. They are used in a conventional manner, for example by watering, immersion, spraying, atomizing, misting, vaporizing, injecting, slurrying, brushing on, dusting, scattering, dry dressing, moist dressing, wet dressing, slurry dressing or encrusting.

In the treatment of parts of plants, the concentrations of active ingredient in the use forms can be varied within a substantial range. They are in general between 1 and 0.0001% by weight, preferably between 0.5 and 0.001% by weight.

In the treatment of seed, amounts of active ingredient of from 0.001 to 50 g per kg of seed, preferably 0.01 to 10 g, are generally required.

In the treatment of the soil, concentrations of active ingredient of 0.00001 to 0.1% by weight, preferably of 0.0001 to 0.02% by weight, are required at the place of action.

EXAMPLE 1

12.0 g (0.06 mole) of 2-bromo-2-nitropropane-1,3-diol, 3.71 g (0.06 mole) of boric acid and 4.69 g (0.06 mole) of 2-mercaptoethanol in 150 ml of benzene were initially taken in a reaction flask, the reaction mixture was heated to the boil, and the resulting water of reaction (3.15 ml) was removed by means of a water separator. 22.93 g (0.06 mole) of tricyclohexyl-tin hydroxide were then added to the solution, which had been cooled to slightly below the boiling point, and the reaction mixture was heated further, another 1.1 ml of water being separated off. When the water of reaction had been completely removed, the solvent was distilled off in vacuo.

38.0 g of 2-[2-tricyclohexyltinthia]-oxyethyl-5-bromo-5-nitro-1,3,2-dioxaborinane were obtained as a viscous oil.

EXAMPLE 2

18.0 g (0.09 mole) of 2-bromo-2-nitropropane-1,3-diol, 5.56 g (0.09 mole) of boric acid and 33.0 g (0.09 mole) of triphenyl-tin hydroxide in 350 ml of chloroform were initially taken in a reaction flask, the reaction mixture was heated to the boil, and the resulting water of reaction was removed by means of a water separator. When the water of reaction (4.9 ml) had been completely removed, the solvent was distilled off in vacuo.

50.1 g of 2-triphenyltinoxy-5-bromo-5-nitro-1,3,2-dioxaborinane were obtained as a viscous oil.

EXAMPLE 3

4.0 g (0.02 mole) of 2-bromo-2-nitropropane-1,3-diol, 1.23 g (0.02 mole) of boric acid and 11.35 g (0.01 mole) of bis-(trineophyltin) oxide in 120 ml of toluene were initially taken in a reaction flask, the reaction mixture was heated to the boil, and the water of reaction was removed by means of a water separator.

After the solvent had been stripped off in vacuo, 14 g of 2-trineophyltinoxy-5-bromo-5-nitro-1,3,2-dioxaborinane were obtained as a viscous oil.

$^1$H-NMR(CDCl$_3$): z=4.59 ppm, $f_A - f_B$=52.4 Hz.

EXAMPLE 4

1.84 g (0.0136 mole) of 2-methyl-2-nitropropane-1,3-diol, 0.84 g (0.0136 mole) of boric acid and 5.7 g (0.0068 mole) of bis-(tricyclohexylmethyltin) oxide in 100 ml of xylene were initially taken in a reaction flask, the reaction mixture was heated to the boil, and the water of reaction (0.6 ml) was removed by means of a water separator.

After the solvent had been stripped off in vacuo, 7.6 g of 2-tricyclohexylmethyltinoxy-5-methyl-5-nitro-1,3,2-dioxaborinane were obtained as a viscous oil. $^1$H-NMR(CDCl$_3$): z=4.32 ppm, $f_A - f_B$=6.62 Hz.

EXAMPLE 5

4.47 g (0.03 mole) of 2-ethyl-2-nitropropane-1,3-diol, 1.85 g (0.03 mole) of boric acid and 2.34 g (0.03 mole) of 2-mercaptoethanol in 80 ml of benzene were initially taken in a reaction flask, the reaction mixture was heated to the boil, and the water of reaction (1.9 ml) was removed by means of a water separator. 3.71 g (0.015 mole) of dibutyl-tin oxide were then added to the solution, which had been cooled to slightly below the boiling point, and the reaction mixture was heated further, another 1.1 ml of water being formed and being separated off.

After the solvent had been removed, 10.0 g of bis-[β-(5-ethyl-5-nitro-1,3,2-dioxaborinan-2-yl-oxy)ethylthio]-dibutyl tin were obtained as a viscous oil. $^1$H-NMR(CDCl$_3$): z=4.45 ppm, $f_A - f_B$=60.4 Hz.

EXAMPLE 6

4.0 g (0.02 mole) of 2-bromo-2-nitropropane-1,3-diol, 1.23 g (0.02 mole) of boric acid and 3.6 g (0.01 mole) of dioctyl-tin oxide in 100 ml of petroleum ether were initially taken in a reaction flask, the reaction mixture was heated to the boil, and the water of reaction (0.9 ml) was removed by means of a water separator.

After the solvent had been evaporated in vacuo, 7.8 g of bis-[((5-bromo-5-nitro-1,3,2-dioxaborinan)-2-yl)-oxy]-dioctyl tin were obtained as a viscous oil.

EXAMPLE 7

9.71 g (0.015 mole) of bis-(dibutylcyclohexyltin) oxide, 1.85 g (0.03 mole) of boric acid and 6.0 g (0.03 mole) of 2-bromo-2-nitropropane-1,3-diol in 100 ml of benzene were initially taken in a reaction flask, the reaction mixture was heated to the boil, and the water of reaction (1.35 ml) was removed by means of a water separator.

After the solvent had been removed in vacuo, 16.1 g of 2-cyclohexyldibutyltinoxy-5-bromo-5-nitro-1,3,2-dioxaborinane were obtained as a viscous oil. $^1$H-NMR(CDCl$_3$): z=4.61 ppm, $f_A - f_B$=46.8 Hz.

The following compounds were obtained by one of the stated methods:

| | n | $R_1$ | Y | $(Z)_{4-n}$ | | z (ppm) | $f_A - f_B$ (Hz) | LM |
|---|---|---|---|---|---|---|---|---|
| 8 | 1 | Br | O | (n-Butyl)$_3$ | Oil | 4.63 | 47.9 | CDCl$_3$ |
| 9 | 1 | Br | O | (Cyclohexyl)$_3$ | Oil | 4.64 | 48.8 | CDCl$_3$ |
| 10 | 1 | CH$_3$ | O | (Cyclohexyl)$_3$ | 65–67° C. | 4.34 | 63.5 | CDCl$_3$ |
| 11 | 1 | CH$_3$ | O | (Neophyl)$_3$ | Oil | 4.32 | 66.9 | CDCl$_3$ |
| 12 | 1 | CH$_3$ | OC$_2$H$_4$S | (Cyclohexyl)$_3$ | 122–125° C. | 4.39 | 63.5 | CDCl$_3$ |
| 13 | 1 | CH$_3$ | OC$_2$H$_4$S | (Neophyl)$_3$ | Oil | 4.35 | 65.7 | CDCl$_3$ |
| 14 | 1 | C$_2$H$_5$ | O | (n-Butyl)$_3$ | Oil | 4.36 | 61.4 | CDCl$_3$ |
| 15 | 1 | C$_2$H$_5$ | O | (Phenyl)$_3$ | Oil | | | |
| 16 | 1 | C$_2$H$_5$ | O | (Cyclohexyl)$_3$ | Oil | 4.36 | 63.5 | CDCl$_3$ |
| 17 | 1 | C$_2$H$_5$ | OC$_2$H$_4$S | (n-Butyl)$_3$ | Oil | 4.45 | 64.3 | CDCl$_3$ |
| 18 | 1 | C$_2$H$_5$ | OC$_2$H$_4$S | (Phenyl)$_3$ | Oil | 4.16 | 72.6 | CDCl$_3$ |
| 19 | 1 | C$_2$H$_5$ | OC$_2$H$_4$S | (Cyclohexyl)$_3$ | Oil | 4.42 | 62.9 | CDCl$_3$ |
| 20 | 1 | C$_2$H$_5$ | OC$_2$H$_4$S | (Neophyl)$_3$ | Oil | 4.36 | 66.5 | CDCl$_3$ |
| 21 | 1 | C$_3$H$_7$ | O | (Cyclohexyl)$_3$ | 72–74° C. | 4.37 | 61.9 | CDCl$_3$ |
| 22 | 1 | C$_3$H$_7$ | OC$_2$H$_4$S | (Cyclohexyl)$_3$ | Oil | 4.41 | 61.4 | CDCl$_3$ |
| 23 | 1 | C$_4$H$_9$ | OC$_2$H$_4$S | (Cyclohexyl)$_3$ | Oil | 4.41 | 62.4 | CDCl$_3$ |
| 24 | 1 | C$_5$H$_{11}$ | OC$_2$H$_4$S | (Cyclohexyl)$_3$ | Oil | 4.41 | 61.4 | CDCl$_3$ |
| 25 | 1 | C$_7$H$_{15}$ | OC$_2$H$_4$S | (n-Butyl)$_3$ | Oil | 4.44 | 64.5 | CDCl$_3$ |
| 26 | 1 | C$_7$H$_{15}$ | OC$_2$H$_4$S | (Phenyl)$_3$ | Oil | 4.22 | 71.6 | CDCl$_3$ |
| 27 | 1 | henyl | O | (Cyclohexyl)$_3$ | 55–59° C. | 4.81 | 65.5 | CDCl$_3$ |
| 28 | 1 | Br | OC$_2$H$_4$S | (n-Butyl)$_3$ | Oil | | | |
| 29 | 1 | Br | OC$_2$H$_4$S | (Phenyl)$_3$ | Oil | 4.44 | 59.2 | CDCl$_3$ |
| 30 | 1 | C$_2$H$_5$ | O | (Norbornyl)$_3$ | 92–99° C. | 4.35 | 62.4 | CDCl$_3$ |
| 31 | 1 | Br | O | (Norbornyl)$_3$ | 139–142° C. | 4.62 | 48.5 | CDCl$_3$ |
| 32 | 1 | C$_2$H$_5$ | O | (Neophyl)$_3$ | Oil | 4.34 | 66.5 | CDCl$_3$ |
| 33 | 1 | C$_3$H$_7$ | O | (Neophyl)$_3$ | Oil | 4.32 | 66.5 | CDCl$_3$ |
| 34 | 1 | Br | OC$_2$H$_4$S | (Neophyl)$_3$ | Oil | 4.60 | 50.0 | CDCl$_3$ |
| 35 | 1 | Br | O | (Cyclohexylmethyl)$_3$ | Oil | 4.60 | 47.5 | CDCl$_3$ |
| 36 | 1 | CH$_3$ | O | (Butyl)$_2$ Cyclohexyl | Oil | 4.33 | 60.4 | CDCl$_3$ |
| 37 | 1 | Br | OC$_6$H$_4$S | (Cyclohexyl)$_3$ | Oil | 4.38 | 41.0 | CDCl$_3$ |
| 38 | 1 | CH$_3$ | OC$_6$H$_4$S | (Cyclohexyl)$_3$ | Oil | 4.36 | 60.2 | CDCl$_3$ |
| 39 | 1 | Br | OC$_6$H$_4$S | (Phenyl)$_3$ | Oil | 4.46 | 51.0 | CDCl$_3$ |
| 40 | 2 | Br | O | (Phenyl)$_2$ | Oil | | | |
| 41 | 2 | C$_2$H$_5$ | O | (Phenyl)$_2$ | Oil | | | |
| 42 | 2 | C$_2$H$_5$ | O | (n-Octyl)$_2$ | Oil | | | |
| 43 | 2 | Br | OC$_2$H$_4$S | (n-Butyl)$_2$ | Oil | | | |
| 44 | 2 | Br | OC$_2$H$_4$S | (n-Octyl)$_2$ | Oil | | | |
| 45 | 2 | C$_2$H$_5$ | OC$_2$H$_4$S | (n-Octyl)$_2$ | Oil | 4.43 | 59.4 | CDCl$_3$ |
| 46 | 2 | Br | OC$_2$H$_4$S | (Phenyl)$_2$ | Oil | 4.32 | 16.2 | CDCl$_3$/CD$_3$OD |
| 47 | 2 | C$_2$H$_5$ | OC$_2$H$_4$S | (Phenyl)$_2$ | Oil | | | |
| 48 | 1 | CH$_3$ | O | (Neopentyl)$_3$ | 64–68° C. | | | |
| 49 | 1 | iso-Butyl | O | (Phenyl)$_3$ | 125–132° C. | 4.33 | 63.1 | CDCl$_3$ |
| 50 | 1 | CH$_3$ | O | (Norbornyl)$_3$ | 147–152° C. | | | |

EXAMPLE 51

20 parts by weight of the compound described in Example 2 were mixed with 70 parts by weight of attapulgite and 10 parts by weight of Na oleylmethyltauride (about 33% strength) and the mixture was very finely milled in a pinned disk mill, a wettable powder being obtained. When the powder was stirred into water, a suspension suitable for application was formed.

EXAMPLE 52

50 parts by weight of the compound 15 were mixed with 41 parts by weight of a highly disperse silica, 6 parts by weight of Na oleylmethyltauride (about 33% strength) and 3 parts by weight of Na diisobutylnaphthalenesulfonate, and the mixture was then milled for 4 hours in a ball mill, a wettable powder being formed. When the powder was stirred into water, a suspension suitable for application was formed.

EXAMPLE 53

20 parts by weight of the compound described in Example 1 were dissolved in methylene chloride, 70 parts by weight of attapulgite were added and the solvent was evaporated. 10 parts by weight of Na oleylmethyltauride (about 33% strength) were added to the residue, and the mixture was milled for 4 hours in a ball mill, a wettable powder being formed. When the powder was stirred into water, a suspension suitable for application was formed.

EXAMPLE 54

Polyoxyethylene sorbitan tall oil ester was added to 20 parts by weight of the compound 17 in a mixture of 35 parts by weight of dimethylformamide, 35 parts by weight of xylene and 10 parts by weight of an alkylarylsulfonate, an emulsion concentrate being formed. When the latter was stirred into water, an emulsion suitable for application was formed.

EXAMPLE A

In vitro Tests

Agar nutrient media having the following compositions were used in in vitro tests:
Nutrient medium I: consisting of agar and oatmeal
Nutrient medium II: consisting of agar, biomalt, wood powder and peptone
Nutrient medium III: consisting of agar, biomalt and peptone=5% strength malt extract agar
Nutrient medium IV: consisting of agar, glucose, oats extract and peptone.

Aqueous dispersions of 0.5%, 0.2%, 0.04%, 0.008% and 0.0016% were prepared from the formulations of active ingredient. Filter paper disks 5 mm in diameter were soaked in these dispersions and then were laid on the inoculated nutrient medium. In this way, *Botrytis* cinerea, Aspergillus niger, Alternaria tenuis, Penicillium glaucum, Trichoderma viridae and Xanthomonas spp. were tested. In testing Merulius lacrimans, Polystictus cinnabarinus, Polyporus vaporarius, Coniophora puteana, Poria placenta and Rhizoctonia solani, the aqueous dispersions of active ingredient were added directly to the nutrient medium which had been cooled to 40° C., and were adjusted to concentrations of 0.5%, 0.2%, 0.04%, 0.008% and 0.0016%.

Alternaria tenuis and Trichoderma viridae were grown in nutrient medium I, Merulius lacrimans, Polystictus cinnabarinus and Polyporus vaporarius were grown in nutrient medium II, Botrytis cinerea, Aspergillus niger, Coniophora puteana, Penicillium glaucum, Poria placenta and Rhizoctonia solani were grown in nutrient medium III, and Xanthomonas spp. was grown in nutrient medium IV.

The growth of the following cultures was prevented by, for example, the following compounds in a concentration of 0.0016%:
Alternaria tenuis by compound 14,
Aspergillus niger by the compounds 10,16,17 and 19,
Botrytis cinerea by compound 14,
Penicillium glaucum by the compounds 14 and 15,
Polyporus vaporarius by compound 14,
Merulius lacrimans by compound 14
Trichoderma viridae by the compounds 8,14,24 and 25 and
Xanthomonas spp. by compound 14.

For example, the compound 14 in a concentration of 0.008% prevented the growth of Rhizoctonia solani.

EXAMPLE B

Action of the Substances Against *Pseudocercosporella herpotrichoides* in the Plate Test Filter paper disks were soaked in aqueous dispersions of the formulated active ingredients which contained 0.2% of active ingredient. These disks were then laid on oatmeal agar nutrient media which had been inoculated beforehand with mycelia of *Pseudocercosporella herpotrichoides*. The dishes were then incubated for 3 days at 5° C., after which they were kept at 22° C. in artificial light. After 12 days, the control was completely covered with mycelia. The evaluation was carried out at this point by determining the diameter of the inhibitory areola. An inhibitory areola diameter larger than 1 cm was measured, for example, for the compounds 14, 28 and 25.

EXAMPLE C

Effect of the Active Ingredients on the Growth of the Alga *Chlorella fusca*

The substance to be tested, dissolved in acetone, was added to 70 ml of algae suspension, corresponding to 0.1 mg of algae per ml of nutrient solution. The algae suspensions were aerated for 48 hours in artificial light. The percentage P was evaluated, this being the algae concentration (in mg) in the test solution as a ratio to that in the control (=100%). At a concentration of active ingredient of 5 ppm, for example, the compound according to Example 2 and the compounds 15 and 26 gave percentages less than 1.

EXAMPLE D

Action of the Substances Against *Plasmopora viticola* on Vine Cuttings in the Greenhouse Young potted vines of the "Gruner Veltliner" variety with 3 to 6 foliage leaves were sprayed, until dripping wet, with a 0.01% strength aqueous dispersion of the formulated active ingredient. The plants remained in a greenhouse at 20° C. and about 70% relative humidity until the spray coating had dried. The vines were then inoculated with an aqueous spore suspension of the fungus *Plasmopora viticola*. The plants injected in this manner were then kept in the dark in a moist chamber for 48 hours at 18° C. and 95% relative humidity, after which they were placed in climatic chambers with high relative humidity. When the disease had broken out on the leaves of the control plants, the infestation with *Plasmopora viticola* was determined. For example, the compounds 26 and 49 were able to achieve 100% inhibition of the outbreak of the disease.

EXAMPLE E

Efficiency Against *Helminthosporium gramineum* When Used as a Dressing (Open Air Test)

Barley seed (spring barley) naturally infected with stripe disease was carefully dressed with 30 g of active ingredient per 100 kg of seed, and cultivated on 2 m² plots in two applications. Evaluation was carried out by counting the number of diseased plants at the time of sprouting.

$$\text{Efficiency in \%} = \frac{\text{number of diseased plants among treated ones}}{\text{number of diseased plants among untreated ones}} \times 100$$

For example, the compounds 8, 14 and 28 reached an efficiency of 100%.

EXAMPLE F

Action Against *Septoria apii* on Celery Plants

Potted celery plants in the 5-leaf to 6-leaf stage were wetted all over with the aqueous dispersions of the formulated test substances. When the spray coating had dried, the plants were inoculated with spores obtained from infected plants, this being done by spraying these spores in the form of a suspension. The plants were then incubated in a climatic chamber at about 18° C. and a relative humidity as high as possible, and fungal infestation was evaluated after 14 days. At a concentration of 0.005%, the compound according to Example 2 and the compounds 8, 14, 17 and 28 were able to effect 100% inhibition of the outbreak of disease.

EXAMPLE G

Contact Action Against *Tetranychus urticae* (Adult)

The primary leafs of the kidney bean (*Phaseolus vulgaris*) were brought into contact, 48 hours before the beginning of the test, with an infested leaf from the mass culture of *Tetranychus urticae*. These plants were then sprayed, until dripping wet, with aqueous dispersions of the formulated active ingredients, after which they were left to stand in a greenhouse at about 23° C. 24 hours after the treatment, all mobile stages were evaluated under the microscope with regard to living and dead individuals. At a concentration of 0.001%, for example, the compound according to Example 4 and the compounds 10, 16, 19, 23, 24, 30, 37 and 48 had a 100% effect.

EXAMPLE H

Contact Action Against *Aphis fabae* on Celery

Potted celery plants (*Apium graveolens*) thoroughly infested with *Aphis fabae* were sprayed, until dripping wet, with an aqueous dispersion of the formulated active ingredient, and then placed in a greenhouse at about 23° C. 24 hours after the treatment, evaluation in respect of dead and living individuals was carried out under the microscope. At a concentration of active ingredient of 0.05%, for example, the compounds 8, 14, 17, 28 and 48 achieved 100% success in control.

EXAMPLE I

Insecticidal Contact Action

Determination of the LD50 values for *Drosophila melanogaster*, *Musca domestica*, *Blattella germanica* and *Calandra granaria*

The active ingredients were dissolved in acetone to give solutions of the stated concentrations, and the solutions were sprayed into Petri dishes of 10 cm diameter. When the spray coating had dried on, the individual insects were added, and the Petri dishes were placed upside down on filter paper. After 24 hours in the case of *Drosophila melanogaster* and *Musca domestica*, and after 48 hours in the case of *Blattella germanica* and *Calandra granaria*, the dead and living individuals were counted.

The Table shows the active ingredients and the concentrations at which the LD50 value was reached.

| No. | Blattella germanica | Calandra granaria | Drosophila melanogaster | Musca domestica |
|---|---|---|---|---|
| 17 | 0.05% | 0.075% | 0.05% | — |
| 14 | 0.25% | — | 0.025% | — |
| 28 | 0.25% | 0.1% | 0.05% | — |
| 8 | 0.5% | 0.25% | 0.05% | — |
| 10 | — | — | 0.1% | — |
| 9 | — | — | 0.25% | — |
| 21 | — | — | 0.25% | 0.1% |
| 16 | — | — | — | 0.1% |

EXAMPLE J

Action Against Larvae of *Blutella Xylostella*

Cabbage leaves were dipped for 10 seconds into the aqueous solution of the formulated active ingredient and, after the coating had dried on, were introduced into Petri dishes together with the larvae of *Blutella Xylostella*. After 7 days, the dead and living individuals were counted. For example, the compound No. 9 gave the following values:

| Concentration (ppm) | % mortality after 7 days |
|---|---|
| 250 | 100 |
| 125 | 95 |
| 62.5 | 95 |
| 31.3 | 55 |

What we claim is:
1. A 1,3,2-dioxaborinane of the formula:

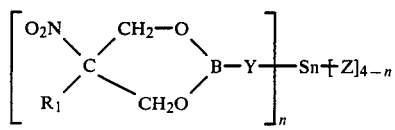

wherein $R_1$ is a straight-chain or branched alkyl group having 1 to 20 carbon atoms, a phenyl group or bromine, Y is a 1-oxy-2-thioethyl group, a 1-oxy-4-thiophenyl group or oxygen, each group Z independently of the others is a straight-chain or branched alkyl group having 1 to 20 carbon atoms, a cycloalkyl, bicycloalkyl or cycloalkylalkyl group, a phenyl group or a phenylalkyl group, and n is the number 1 or 2.

2. A compound according to claim 1, wherein $R_1$ is a straight-chain or branched alkyl group having 1 to 10 carbon atoms.

3. A compound according to claim 2, wherein $R_1$ is a straight-chain or branched alkyl group having 1 to 5 carbon atoms.

4. A compound according to claim 1, wherein $R_1$ is bromine.

5. A compound according to claim 1, wherein Y is oxygen.

6. A compound according to claim 1, wherein Z is a cycloalkyl group.

7. A compound according to claim 1, wherein Z is a bicycloalkyl group.

8. A compound according to claim 1, wherein Z is a cycloalkylalkyl group.

9. A compound according to claim 1, wherein Z is a phenylalkyl group.

10. A compound according to claim 1, wherein Z is a phenyl group.

11. A compound according to claim 1, wherein Z is a straight chain or branched alkyl group having 1 to 10 carbon atoms.

12. A compound according to claim 1, wherein n is the number 1.

13. A biocidal agent, having fungicidal and algicidal activity or insecticidal and acaricidal activity, which contains a 1,3,2-dioxaborinane of the formula:

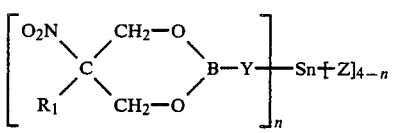

wherein $R_1$ is a straight-chain or branched alkyl group having 1 to 20 carbon atoms, a phenyl group or bromine, Y is a 1-oxy-2-thioethyl group, a 1-oxy-4-thiophenyl group or oxygen, each group Z independently of the others is a straight-chain or branched alkyl group having 1 to 20 carbon atoms, a cycloalkyl, bicycloalkyl or cycloalkylalkyl group, a phenyl group or a phenylalkyl group, and n is the number 1 or 2.

14. A fungicidal and algicidal agent of the general formula I as claimed in claim 13, wherein the groups $R_1$, Y and Z and the number n have the meaning given in claim 13.

15. An insecticidal and acaricidal agent of the formula I as claimed in claim 13, wherein the groups $R_1$, Y and the number n have the meaning given in claim 13 and each group Z independently of the others is a straight-chain or branched alkyl group having 1 to 20 carbon atoms, a cycloalkyl, bicycloalkyl or cycloalkylalkyl group or a phenylalkyl group.

* * * * *